(12) United States Patent
Sano et al.

(10) Patent No.: US 7,601,363 B2
(45) Date of Patent: *Oct. 13, 2009

(54) SUSTAINED-RELEASE DRUG FORMULATIONS

(75) Inventors: Akihiko Sano, Toyonaka (JP); Masako Kajihara, Itami (JP); Hiroo Maeda, Sakai (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/688,082

(22) Filed: Mar. 19, 2007

(65) Prior Publication Data

US 2007/0166377 A1 Jul. 19, 2007

Related U.S. Application Data

(63) Continuation of application No. 10/089,694, filed as application No. PCT/JP00/07639 on Oct. 31, 2000, now Pat. No. 7,247,312.

(30) Foreign Application Priority Data

Nov. 10, 1999 (JP) .............................. 319108/1999

(51) Int. Cl.
*A61K 9/14* (2006.01)
*A61F 2/00* (2006.01)
*A61F 13/00* (2006.01)

(52) U.S. Cl. ..................... 424/422; 424/423; 424/489; 424/490

(58) Field of Classification Search ........................ None
See application file for complete search history.

(56) References Cited

U.S. PATENT DOCUMENTS 3,279,996 A 10/1966 Long et al.
4,191,741 A 3/1980 Hudson et al.
4,331,651 A 5/1982 Reul et al.
4,346,709 A 8/1982 Schmitt
4,675,189 A 6/1987 Kent et al.
4,985,253 A 1/1991 Fujioka et al.
5,324,519 A 6/1994 Dunn et al.
5,417,985 A 5/1995 Coutel et al.
5,851,547 A 12/1998 Fujioka et al.
5,955,143 A 9/1999 Wheatley et al.
6,120,789 A 9/2000 Dunn
6,210,715 B1 4/2001 Starling et al.
7,247,312 B1 * 7/2007 Sano et al. .................. 424/422

FOREIGN PATENT DOCUMENTS

JP 2818892 B2 8/1998

OTHER PUBLICATIONS

Robertson et al., Contraception, vol. 27, No. 5, pp. 483-495, (1983).
Pfister et al., Proceed. Intern, Symp Control Rel. Bioact. Mater . vol. 12, pp. 145-146, (1985).
Pfister et al., Proceed. Intern, Symp Control. Rel. Bioact. Mater, vol. 14, pp. 223-224, (1987).

* cited by examiner

*Primary Examiner*—S. Tran
(74) *Attorney, Agent, or Firm*—Birch, Stewart, Kolasch & Birch, LLP.

(57) ABSTRACT

The present invention relates to a formulation for implantation having a novel constitution, which accomplishes controlled releases of active ingredients. The formulation comprises one of combinations (a), (b) and (c), as well as a carrier comprising a hydrophobic polymer, wherein the particle combination is dispersed into the carrier: (a) particles comprising an active ingredient, particles comprising a carbonate, and particles comprising a substance which is reacted with the carbonate in an aqueous solution to generate carbon dioxide (substance such as an acid); (b) particles comprising an active ingredient and a carbonate, and particles comprising a substance such as an acid; and (c) particles comprising a carbonate, and particles comprising an active ingredient and a substance such as an acid.

6 Claims, 1 Drawing Sheet

SUSTAINED-RELEASE DRUG FORMULATIONS

This application is a Continuation of co-pending application Ser. No. 10/089,694 filed on Apr. 3, 2002 and for which priority is claimed under 35 U.S.C. § 120. Application Ser. No. 10/089,694 is the national phase of PCT International Application No. PCT/JP00/07639 filed on Oct. 10, 1999 under 35 U.S.C. § 371. The entire contents of each of the above-identified applications are hereby incorporated by reference.

FIELD OF THE INVENTION

The present invention relates to a sustained-release drug formulation, which is directed to long-acting effects of medicines and veterinary medicines.

BACKGROUND OF THE INVENTION

Studies on sustained-release of active ingredients using hydrophobic polymers as carriers of formulations to achieve long-acting effects of medicines, relief of side effects, decrease in frequency of administration, or the like, have been conducted. To control release-rates of active ingredients is one of the most important subjects in these studies, and modifications of the form or the structure of formulations, usage of additives, and so on, have been tried to attain the controlled release [U.S. Pat. No. 3,279,996, Contraception, 27(5), 483-495, 1983, Japanese Patent Publication (kokai) No. 45694/1980, Japanese Patent Publication (kokai) 174007/1987, WO95/17881].

In case of the formulations for in vivo implantation containing hydrophobic polymers in which slightly soluble active ingredients are dispersed, the amount of the released active ingredients during a defined time period is smaller due to the low solubility of the active ingredients in the surrounding body fluid, and therefore, the formulations could not attain an acceptable efficacy of the active ingredients. With respect to such formulations as those containing the active ingredients dispersed in the hydrophobic polymers, and decreasing in the release rate of the active ingredients, the methods for controlling the release rate of the active ingredients, which comprise using, as an additive, mineral oil, glycerol, alcohol, or the like have been reported (Proceed. Intern. Symp. Control. Rel. Bioact. Mater, 14, 223-224(1987), Proceed. Intern. Symp. Control Rel. Bioact. Mater., 12, 145-146 (1985), and Japanese Patent Publication (kokai) No. 100315/1980). The key underlying these methods is to disperse an amphiphilic solvent such as mineral oil, glycerol, or alcohol into the polymers together with the slightly soluble active ingredients to ensure the solubility and the released amount of the active ingredients to be increased. However, the formulations according to these methods may provide diverse release rates, depending on a combination among the slightly soluble ingredients, the additives, and the hydrophobic polymers, and, therefore, are limited to certain practical user.

In case of active ingredients such as live vaccines and inactivated vaccines, which are neither soluble in an organic solvent nor in water, it has been unknown if the active ingredients could be released from the hydrophobic polymer.

SUMMARY OF THE INVENTION

The purpose of the present invention is to provide a formulation for in vivo implantation having a novel constitution which makes possible to control the release rate of active ingredients.

We understood that the conventional methods for promoting the release of the active ingredient by increasing its solubility is limited to certain practical applications, and have struck upon a new concept that in order to accelerate the release of an active ingredient, a protruding force physically derived from the inside of the formulation is produced. Based on the new concept, we continued to investigate, and accomplished the quite novel release-controlling technique, which is applicable to various cases in which sustained-release of active ingredients from hydrophobic polymers is aimed. Specifically, the release-controlling technique comprises incorporating, into a hydrophobic polymer, particles comprising a carbonate and particles comprising a substance which is reacted with the carbonate in an aqueous solution to generate carbon dioxide, together with an active ingredient. The technique is applicable to any kind of active ingredients, and is especially useful for slightly soluble, or insoluble ingredients.

The present invention provides:

(1) a formulation for implantation, which comprises one of particle combinations, which is selected from a group consisting of (a), (b) and (c), as well as a carrier comprising a hydrophobic polymer, wherein the particle combination is dispersed into the carrier:

(a) a particle combination which comprises particles comprising an active ingredient, particles comprising a carbonate, and particles comprising a substance which is reacted with the carbonate in an aqueous solution to generate carbon dioxide;

(b) a particle combination which comprises particles comprising an active ingredient and a carbonate, and particles comprising a substance which is reacted with the carbonate in an aqueous solution to generate carbon dioxide; and (c) a particle combination which comprises particles comprising a carbonate, and particles comprising an active ingredient and a substance which is reacted with the carbonate in an aqueous solution to generate carbon dioxide:

(2) The formulation of item (1), wherein the active ingredient comprises a slightly soluble, or insoluble ingredient.

(3) The formulation of item (2), wherein the insoluble ingredient comprises a live vaccine, or an inactivated vaccine.

(4) The formulation of any one of item (1)-(3), wherein the hydrophobic polymer comprises a polymer which is non-biodegradable.

(5) The formulation of item 4, wherein the hydrophobic polymer comprises silicone.

When the formulation of the invention is administered to the body, the body fluid infiltrates into the formulation to dissolve at least one of the particles comprising the carbonate and the particles comprising the substance which is reacted with the carbonate in an aqueous solution to generate carbon dioxide, and induces the reaction between them, thereby leading to internal generation of the carbon dioxide gas from the formulation. The force for the gas to protrude toward the outside of the formulation accelerates the release of the active ingredients within the formulation. That is, the invention is applicable to an insoluble ingredient, since the release rate is accelerated irrespective of the solubility of the active ingredient in the body fluid according to the invention.

DETAILED DESCRIPTION OF THE INVENTION

Figure 1:
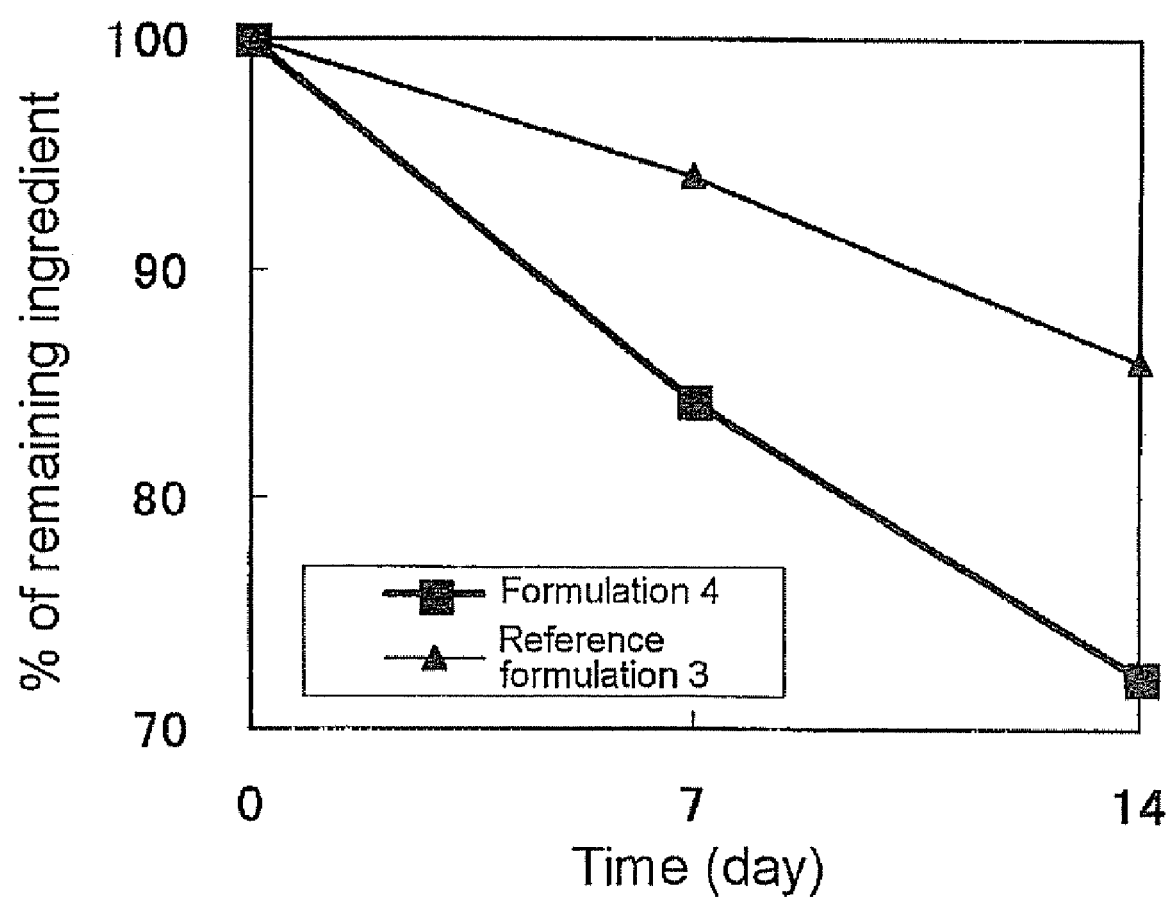
FIG. 1 contains the results of Test example 2, and depicts a graph which shows the decrease in the percentage of the remaining ivermectin in the formulations of the present invention, which were subcutaneously administered to mice. Formulation 4 of the present invention was prepared according to Example 4, whereas reference formulation 3 was prepared according to Reference 3.

More specifically, the present invention is characterized by the events that (1) when the formulation is administered to the body, the body fluid infiltrates into the formulation to dissolve at least one of the particles comprising the carbonate and the particles comprising the substance which is reacted with the carbonate in an aqueous solution to generate carbon dioxide, and both are reacted so as to generate internally the carbon dioxide gas from the formulation; and (2) the pressure force of the generated carbon dioxide gas puts the active ingredient dispersed in the formulation toward the outside, which events accelerate the release of the active ingredients. Further, the gas pressure creates a fine crack within the formulation so that infiltration rate of water into the formulation increases, leading to accelerating of the release of the active ingredients. Under the circumstances, the invention is especially useful for slightly soluble ingredients, of which release rate is slower, and insoluble ingredients. According to the invention, the pressure force which protrude the active ingredient toward the outside of the formulation, and the crack formation can be modified depending on an amount and a rate of the generated gas, by selecting a combination or contents between a carbonate and a substance which is reacted with the carbonate in an aqueous solution to generate carbon dioxide, and therefore, the invention makes possible the control of the release rate of active ingredients.

As a preferred substance for "a substance which is reacted with a carbonate in an aqueous solution to generate carbon dioxide" used in a combination with a carbonate is an acid as described below, the substance may be abbreviated as "a substance(s) such as an acid(s)" if necessary.

An active ingredient, a carbonate, and a substance such as an acid which are comprised in the formulation of the present invention can be combined in a manner of any one of the followings (a), (b) and (c):

(a) particles comprising an active ingredient, particles comprising a carbonate, and particles comprising a substance such as an acid;

(b) particles comprising an active ingredient and a carbonate, and particles comprising a substance such as an acid;

(c) particles comprising a carbonate, and particles comprising a substance such as an acid and an active ingredient.

In general, the carbonate is alkaline whereas the substance such as an acid are acidic. The combination thereof may be selected in light of pH stability of the active ingredient.

Particles comprising an active ingredient, particles comprising a carbonate, particles comprising a substance such as an acid, particles comprising an active ingredient and a carbonate, and particles comprising a substance such as an acid and an active ingredient (hereinafter, these are generally abbreviated as "particles comprising an active ingredient, etch") may comprise solely the active ingredient, the carbonate, the substance such as an acid, the active ingredient and the carbonate, and the substance such as an acid and the active ingredient, respectively, or they can include one or more physiologically acceptable additive(s) such as an excipient, a stabilizing agent, a solubilizing agent, a preservative, and a soothing agent.

Each of the particles comprising an active ingredient, etch, is not limited to any particular species as long as it can be formed into a solid powder. The particles may be those which maintain the solid form in the formulation at a body temperature of animals (preferably mammals) or human to be administered. In particular, the particles preferably maintain the solid form at the body temperature which is higher than the normal temperature of animals or human by at least about 1° C., and when a disease to be treated is associated with a high fever, the particles need to maintain the particulate solid form at the much higher temperature than the normal temperature.

Specifically, the temperature which is higher than the normal body temperature of animals or human by at least about 1° C. is exemplified generally by 38° C. in case of the formulation to be administered to human, 43° C. in case of the formulation used in the human diseases associated with a high fever, 40° C. in case of the formulation to be administered to animals (for example dog, cat, pig, cattle), and 45° C. in case of the formulation used in the animal diseases associated with a high fever.

The body temperature of animals is described in for example RINSHO KACHIKU NAIKA SHINDAN-GAKU (Rhoichi Nakamura, Yokendo, Japan, 1982), and it is possible to determine the minimum temperature to maintain the solid form, referring to such documents.

Considering the body temperatures determined as shown above, the particles comprising an active ingredient, etc., which maintain the solid form at 50° C., could be applied to most animals or human.

Hydrophobic polymer is not limited to any particular polymer as long as it is biocompatible, and one of the hydrophobic polymers can be used solely, or in combination with one or more of other kinds of the polymers. The hydrophobic polymers are roughly divided into a non-biodegradable and biodegradable polymers, and are exemplified by the following, but are not limited to them. The non-biodegradable hydrophobic polymers include silicones, ethylene-vinyl acetate copolymers, polyethylenes, polypropylenes, polytetrafluoroethylenes, polsyurethanes, polyacrylates, polymethacrylates, and any others. Preferably, silicones, more preferably, Silastic® Medical Grade ETR Elastomer Q7-4750 or Dow Corning® MDX 4-4210 Medical Grade Elastomer, and the like are employed. Biodegradable hydrophobic polymers are exemplified by polyesters, poly-amino acids, polyanhydrides, and the like, including poly(lactic acid-glycolic acid) copolymers (PLGA), polylactic acids, and any others.

Carbonate is not limited to any particular species as long as it is physiologically acceptable and is reacted with a substance such as an acid in an aqueous solution to generate carbon dioxide, and the carbonate may be generally reacted in an acidic condition to generate carbon dioxide. Specifically, carbonates are exemplified by sodium hydrogen carbonate, sodium carbonate, potassium carbonate, potassium hydrogen carbonate, ammonium carbonate, lithium carbonate, and the like, but not limited to them. Preferably, sodium carbonate, or sodium hydrogen carbonate is employed. Any one of the carbonates can be employed solely, or in combination with one or more is other kind of the carbonates.

Substance which is reacted with the carbonate in an aqueous solution to generate carbon dioxide (substance such as an acid) is not limited to any particular species as long as the substance is physiologically acceptable and is reacted with the carbonate to generate carbon dioxide. Specifically, the substance includes an acid, and more specifically, it includes, but not limited to, an organic acid such as citric acid, tartaric acid, malic acid, gluconic acid, fumaric acid, itaconic acid, phtalic acid, lactic acid, ascorbic acid, and an inorganic acid salt such as sodium dihydrogenphosphate, potassium dihydrogenphosphate, and an inorganic acid such as boric acid. It is preferable to employ citric acid or tartaric acid. Any one of the substances can be employed solely, or in combination with one or more other kind of the substances.

Either the carbonates or the substances such as an acid should be water-soluble.

Active ingredient is not limited to any particular species as long as it is physiologically acceptable, and, it can be preferably slightly soluble or insoluble according to the invention. Any one of the slightly soluble or insoluble ingredients can be employed solely, or in combination with one or more other kind of the ingredients. Further, any combinations of the slightly soluble and the water-soluble ingredients, or the insoluble and the water-soluble ingredients, or the slightly soluble, the insoluble and the water-soluble ingredients can be employed.

"Slightly soluble" as referred herein with respect to a ingredient means that the solubility of the ingredient in water is low, and, for example, the criteria that the solubility in water is "practically insoluble" (the amount of solvent required to dissolve 1 g or 1 ml of a solute is 10,000 ml or more), "very slightly soluble" (the amount of solvent required to dissolve 1 g or 1 ml of a solute is from 1000 ml to 10,000 ml), and "slightly soluble" (the amount of solvent required to dissolve 1 g or 1 ml of a solute is from 100 ml to 1,000 ml), referring to Japanese Pharmacopoeia 13th revision (1996), may be used.

The slightly soluble ingredient is exemplified by antibiotics such as avermectin, ivermectin, and spiramycin; antibacterials such as amoxycillin, erythromycin, oxytetracycline, and lincomycin; anti-inflammatory agents such as dexamethasone, and phenylbutazone; hormones such as levothyroxine; corticosteroids such as dexamethasone palmitate, triamcinolone acetonide, and halopredone acetate; nonsteroidal anti-inflammatory agents such as indomethacin, and aspirin; agents for treating artery occlusion such as prostaglandin $E_1$; anticancer agents such as actinomycin, and daunomycin; agents for treating diabetes such as acetohexamide; agents for treating bone diseases such as estradiol. The active ingredients include not only an agent having a therapeutic activity, but also an agent having, supporting, or inducing a physiological activity, such as Vitamin $D_3$, or an adjuvant used in a vaccine, which includes hydrophobic adjuvants such as muramyl dipeptide.

As "Water-soluble" as referred herein, the criteria that the solubility in water is "sparingly soluble" (the amount of solvent required to dissolve 1 g or 1 ml of a solute is from 30 ml to 100 ml), "soluble" (the amount of solvent required to dissolve 1 g or 1 ml of a solute is from 10 ml to 30 ml), "freely soluble" (the amount of solvent required to dissolve 1 g or 1 ml of a solute is from 1 ml to 10 ml), or "very soluble" (the amount of solvent required to dissolve 1 g or 1 ml of a solute is less than 1 ml) according to Japanese Pharmacopoeia 13th revision (1996), may be used.

The water-soluble ingredient is exemplified by cytokines such as interferons, and interleukins; hematopoietic factors such as colony-stimulating factors, and erythropoietin; hormones such as growth hormone, growth hormone releasing factor, calcitonin, luteinizing hormone, luteinizing hormone releasing hormone, and insulin; growth factors such as somatomedin, nerve growth factor, neurotrophic factors, fibroblast growth factor, and hepatocyte growth factor; cell adhesion factors; immunosuppressants; enzymes such as asparaginase, superoxide dismutase, tissue plasminogen activating factor, urokinase, and prourokinase; blood coagulating factors such as blood coagulating factor VIII; proteins involved in bone metabolism such as BMP (bone Morphogenetic Protein); antigens which can be used in vaccines for human and/or animals; adjuvants; cancer antigens; nucleic acids; antibodies; anticancer agents such as adriamycin, bleomycin, mitomycin, fluorouracil, peplomycin sulfate, daunorubicin hydrochloride, hydroxyurea, neocarzinostatin, sizofuran, sodium estramustine phosphate, carboplatin, phosphomycin, ceftiofur sodium, ceftiofur hydrochloride; antibiotics; anti-inflammatory agents; and alkylating agents. The interferons as referred herein may be $\alpha$, $\beta$, $\gamma$, or any other interferons or any combination thereof. Likewise, the interleukin may be IL-1, IL-2, IL-3, or any others, and the colony-stimulating factor may be multi-CSF (multipotential CSF), GM-CSF (granulocyte-monocyte macrophage CSF), G-CSF (granulocyte CSF), M-CSF (monocyte macrophage CSF), or any others.

"Insoluble" with respect to an ingredient means the property of the ingredient which cannot be dissolved in water.

Examples of the insoluble ingredients include vaccines (live vaccine, inactivated vaccine) containing viruses or bacteria. The insoluble substances include not only an ingredient having a therapeutic activity, but also an ingredient having, supporting, or inducing a physiological activity, such as an adjuvant used in a vaccine, which adjuvant typically includes aluminum hydroxide.

The formulation according to the invention can contain physiologically acceptable additives such as a stabilizing agent, a solubilizing agent, a preservative, and a soothing agent. Further, the formulation can contain an additive which controls the release of an active ingredient. The additive can be incorporated into a carrier, whether or not the additive is added to the particles comprising the active ingredient, etc.

A process for preparing a particle combination comprising an active ingredient and a carbonate comprises, for example, making a homogeneous solution of the active ingredient and the carbonate (an additive may be added, if necessary), drying the solution to give a solid, and then, if desired, breaking up or sieving the solid. The drying method is not limited to any particular method, and may be a drying method which is usually used in drying. The method typically includes a drying by a gas flow with nitrogen, helium, or air; a vacuum-drying; a freeze-drying; spontaneous drying; granulation; spray-drying by a spray-dryer; and a any combination thereof. Particles comprising an active ingredient and a substance such as an acid can be prepared in a manner similar to the above process. In the case that particles comprising an active ingredient, particles comprising a carbonate, and particles comprising a substance such as an acid are separately prepared, the similar process can be applied to the preparation for each particles.

BEST MODE FOR CARRYING OUT THE INVENTION

Release rate of an active ingredient in the formulation of the present invention can be controlled by the following factors:

(1) chemical or physical property of a carbonate, or a substance such as an acid;

(2) an amount ratio of a carbonate, and a substance such as an acid;

(3) an amount ratio of particles comprising an active ingredient, etc. and other additives in the total amount of the formulation;

(4) particle sizes of particles comprising an active ingredient, etc., and particles of other additives; or the like.

When a carbonate is a stronger base, and when a substance such as an acid is a stronger acid, carbon dioxide gas is generated more vigorously during a short time period. When the amount ratio of the carbonate and the substance such as an acid is equivalent, carbon dioxide gas is generated most efficiently. Total amounts of the particles comprising an active ingredient, etc and the additives are not limited to any particular value as long as they can be dispersed into a carrier, and can be formed into the formulation, and the total amounts of the particles and the additives may be less than 70%, preferably less than 50%, more preferably less than 30% by weight of the whole formulation although depending on chemical and/or physical property of the employed hydrophobic polymer. The content of the active ingredient naturally can be varied depending on the species of the ingredient, the diseases to be treated, and the severity thereof. Particle sizes of the active ingredient, etc. are not limited to any particular size as long as the sizes enable the particles to be dispersed into a carrier and to form the formulation. The sizes may be varied depending on chemical and/or physical property of the used hydrophobic polymer, and are exemplified, for example, by 1,700 μm or less, preferably 500 μm or less, and more preferably 300 μm or less in diameter. When the active ingredient is insoluble, the particle size of the insoluble ingredient may be varied depending on the particle sizes of the active ingredient, etc., and chemical and/or physical property of the used hydrophobic polymer, and the particle size of the insoluble ingredient itself is exemplified by 50 μm or less, preferably 20 μm or less, and more preferably 1 μm or less in diameter.

Shape of the formulation of the present invention may be selected from any type of shapes as long as the formulation can be administered safely into living body, and particularly, include cylindrical, prismatically cylindrical, cylindroid, tabular, and spherical shape. In case of administration with a needle, a cylindrical formulation is preferred. In case of a cylindrical or tabular formulation, the side wall of formulation may be coated with an outer layer comprising only a hydrophobic polymer. In this case, the inner layer may be single, or multiple. In case of the formulation having the multiple-layered inner layers, the layers may be positioned to form concentric circles with a single center, or may be positioned separately to form circles having different centers, in view of the cross section. Each of the multiple-layered inner layers may contain the same active ingredient, or different ingredients. These shapes are particularly described in, for example, Japanese Patent Publication (kokai) No. 187994/1995.

The formulations of the present invention can be prepared, for example, by mixing one of particle combinations which is selected from a group consisting of (a), (b) and (c), with a hydrophobic polymer before curing;

(a) a particle combination which comprises particles comprising an active ingredient, particles comprising a carbonate, and particles comprising a substance which is reacted with the carbonate in an aqueous solution to generate carbon dioxide;

(b) a particle combination which comprises particles comprising an active ingredient and a carbonate, and particles comprising a substance which is reacted with the carbonate in an aqueous solution to generate carbon dioxide;

(c) a particle combination which comprises particles comprising a carbonate, and particles comprising a substance which is reacted with the carbonate in an aqueous solution to generate carbon dioxide, and an active ingredient: and extruding the mixture through a nozzle, or molding the mixture. Curing method is exemplified by a polymerization process such as the preparation of silicone, dissolution in an organic solvent and the subsequent drying, such as the preparation of ethylene-vinyl acetate copolymer, and the like. The outer layer and the inner layer may be prepared separately, or together. For example, a cylindrical formulation with a single center in the cross section can be prepared by initially preparing an inner layer, then coating the layer with a liquid containing dissolved outer layer material, and drying them; or inserting an inner layer into a tube separately prepared from outer layer material; or molding an inner layer in a tube prepared from outer layer material; or simultaneously extruding inner and outer layers using a nozzle. However, the preparation method is not limited to these examples.

For further descriptions of the present invention, the following examples and test examples are presented, but these examples and test examples should not be construed to limit the scope of the invention.

EXAMPLE 1

A model for insoluble ingredients, fluorescence-labeled latex beads (Polyscience; 1 μm diameter) was washed with water, filtered with a 0.22 μm filter, and dried in vacuo. An aqueous solution (3.63 g, 100 mg/ml) of citric acid and 60 mg of the fluorescence-labeled latex beads were mixed together, and the mixture was lyophilized. The lyophilized cake was passed through a 300 μm-mesh sieve to obtain powder 1. Additionally, sodium hydrogen carbonate powder was passed through a 300 μm-mesh sieve to obtain powder 2. On the other hand, both 0.70 g of components A and B of Silastic® Medical Grade ETR Elastomer Q7-4750 were mixed together) and immediately the mixture was kneaded together with 282.25 mg of powder 1 and 317.75 mg of powder 2. The kneaded material was filled in a syringe, extruded through a nozzle with a diameter of 1.6 mm by application of pressure, and allowed to stand at 37° C. for a day so as to cure. This was then cut to obtain formulation 1, of which shape is cylindrical (having a length of 10 mm and a diameter of 1.7 mm).

EXAMPLE 2

Fluorescence-labeled latex beads (Polyscience; 20 μm diameter) was washed with water, filtered with a 0.22 μm filter, and dried in vacuo. An aqueous solution (3.63 g, 100 mg/ml) of citric acid and 60 mg of the fluorescence-labeled latex beads were mixed together, and the mixture was lyophilized. The lyophilized cake was passed through a 300 μm-mesh sieve to obtain powder 3. Then, both 0.70 g of components A and B of Silastic® Medical Grade ETR Elastomer Q7-4750 were mixed together, and immediately the mixture was kneaded together with 282.25 mg of powder 3 and 317.75 mg of powder 2 prepared as in Example 1. The kneaded material was filled in a syringe, extruded through a nozzle with a diameter of 1.6 mm by application of pressure, and allowed to stand at 37° C. for a day so as to cure. This was then cut to obtain formulation 2, of which shape is cylindrical (having a length of 10 mm and a diameter of 1.7 mm).

EXAMPLE 3

According to a method similar to that in Example 1, the kneaded material comprising the Silastic® elastomer containing the fluorescence-labeled latex beads was prepared, and filled in a syringe. On the other hand, both 50 g of components A and B of Silastic® Medical Grade ETR Elastomer Q7-4750 were mixed together, and the mixture was filled in a second syringe. Nozzles having diameters of 1.6 mm and 1.9 mm were used to extrude both elastomers by application of pressure, which are assembled to form concentric circles with a single center so that the fluorescence-labeled latex beads-containing Silastic® elastomer was positioned inside, whereas the Silastic® elastomer was positioned outside. The resulting material was allowed to stand at 37° C. for a day so as to cure, and then cut to obtain formulation 3, of which shape is cylindrical (having a length of 10 mm, a diameter of 2 mm, and an inner layer diameter of 1.6 mm).

Reference 1

Both 0.98 g of components A and B of Silastic® Medical Grade ETR Elastomer Q7-4750 were mixed together. Then, immediately the mixture was kneaded together with 40 mg of fluorescence-labeled latex beads (Polyscience; 1 µm diameter). The kneaded material was filled in a syringe, extruded through a nozzle with a diameter of 1.6 mm by application of pressure, and allowed to stand at 37° C. for a day so as to cure. This was then cut to obtain reference formulation 1, of which shape is cylindrical (having a length of 10 mm and a diameter of 1.7 mm).

Reference 2

Fluorescence-labeled latex beads (Polyscience; 1 µm diameter) was washed with water, filtered with a 0.22 µm filter, and dried in vacuo. An aqueous solution (8.4 g, 100 mg/ml) of glycine and 60 mg of the fluorescence-labeled latex beads were mixed together, and the mixture was lyophilized. The lyophilized cake was passed through a 300 µm-mesh sieve to obtain powder 4. Then, both 0.70 g of components A and B of Silastic® Medical Grade ETR Elastomer Q7-4750 were mixed together, and immediately the mixture was kneaded together with 600 mg of powder 4. The kneaded material was filled in a syringe, extruded through a nozzle with a diameter of 1.6 mm by application of pressure, and allowed to stand at 37° C. for a day so as to cure. This was then cut to obtain reference formulation 2, of which shape is cylindrical (having a length of 10 mm and a diameter of 1.7 mm).

TEST EXAMPLE 1

Each of formulations 1 and 2 prepared in Examples 1 and 2, and each of reference formulations 1 and 2 prepared in References 1 and 2 was respectively placed into 2 ml of phosphate buffer (pH 7.4) containing 0.1% polyoxyethylene polyoxypropylene copolymer (ADEKA® Pluronic, Asahidenka Kogyo, Japan) and 0.01% sodium azide at 37° C., and the tubes containing the formulation and the buffer were shaken gently. The amounts of latex beads released from each formulation were determined by a fluorophotometer (excitation wavelength: 485 nm, emission wavelength: 538 nm) in order to estimate the cumulative released amounts. These results are shown in Table 1 Table 1 reveals that formulations 1, and 2 according to the present invention accomplished acceleration of release of the latex beads, a model for insoluble ingredients, whereas reference formulations 1 and 2 accomplished no or very little release of the latex beads, showing the superiority in effect of the present invention.

TABLE 1

| formulation | cumulative releasing amounts for 15 days (µg/ml) |
|---|---|
| formulation 1 | 32.4 ± 0.8 |
| formulation 2 | 36.7 ± 3.2 |
| reference formulation 1 | 0.0 ± 0.0 |
| reference formulation 2 | 0.1 ± 0.0 |

EXAMPLE 4

One hundred ten mg of ivermectin, 275 mg of sodium hydrogen carbonate, and 275 mg of citric acid, each of which had been ground, and passed through a 212 µm sieve, were thoroughly combined together A portion (600 mg) of the combination was mixed with both 700 mg of components A and B of Silastic® Medical Grade ETR Elastomer Q7-4750, and the mixture was used as material for the inner layer. On the other hand, both 50 g of components A and B of Silastic® Medical Grade ETR Elastomer Q7-4750 were mixed together, and the mixture was used as material for the outer layer. An extruder (the bore of the outer nozzle: 1.9 mm, the bore of the inner nozzle: 1.6 mm), which accomplishes the extruding so that an inner layer can be covered with an outer layer in a manner of concentric circles with a single center, was used to extrude the materials prepared as shown above. The extruded material was allowed to stand at 37° C. so as to cure, and then cut to obtain formulation 4, of which shape is cylindrical (having a length of 5 mm, a diameter of 1.9 mm, and an inner layer diameter of 1.5 mm).

Reference 3

One hundred fifty mg of ivermectin, and 750 mg of sucrose, each of which had been ground, and passed through a 212 µm sieve, were thoroughly combined together. A portion (600 mg) of the combination was mixed with both 700 mg of components A and B of Silastic® Medical Grade ETR Elastomer Q7-4750, and the mixture was used as material for the inner layer. On the other hand, both 50 g of components A and B of Silastic® Medical Grade ETR Elastomer Q7-4750 were mixed together, and the mixture was used as material for the outer layer. An extruder (the bore of the outer nozzle: 1.9 mm, the bore of the inner nozzle: 1.6 mm), which accomplishes the extruding so that an inner layer can be covered with an outer layer in a manner of concentric circles with a single center, was used to extrude the materials prepared as shown above. The extruded material was allowed to stand at a room temperature so as to cure, and then cut to obtain reference formulation 3, of which shape is cylindrical (having a length of 5 mm, a diameter of 2.0 mm, and an inner layer diameter of 1.5 mm).

TEST EXAMPLE 2

Each of formulation 4 prepared in Example 4, and reference formulation 3 prepared in Reference 3 was subcutaneously administered to mice. The animals were sacrificed under ether anesthesia on the analysing day, and the administered formulations were recovered. The formulations were placed into methanol, and ivermectin dissolved in the methanol was determined by a high performance liquid chromatography to estimate the percentage of the remaining ivermectin in the formulations which had been administered in the animals. The results are shown in FIG. 1

FIG. 1 revealed that the percentage of the remaining ivermectin in formulation 4 was decreased more drastically than that of reference formulation 3, showing that the release of ivermectin from formulation 4 was accelerated compared with that of reference formulation 3, and thus demonstrating a superiority of the present invention.

EFFECTS OF THE INVENTION

As described above, the formulations for in vivo implantation according to the present invention provide controlled release rate of active ingredients on the basis of a protruding force physically derived from the inside of the formulation. The present formulations can be applied to any active ingredients regardless of the kind of the active ingredients, and are especially useful for slightly soluble ingredients, or insoluble ingredients.

The invention claimed is:

1. A cured sustained-release formulation for implantation, which comprises one of particle combinations, which is selected from the group consisting of (a), (b) and (c), and a carrier comprising a hydrophobic polymer, wherein the particle combination is dispersed in the carrier:
   (a) a particle combination which comprises particles comprising an active ingredient, particles comprising a carbonate, and particles comprising a substance which reacts with the carbonate in an aqueous solution to generate carbon dioxide;
   (b) a particle combination which comprises particles comprising an active ingredient and a carbonate, and particles comprising a substance which reacts with the carbonate in an aqueous solution to generate carbon dioxide; and
   (c) a particle combination which comprises particles comprising a carbonate, and particles comprising an active ingredient and a substance which reacts with the carbonate in an aqueous solution to generate carbon dioxide; and
   wherein
      (i) the active ingredient is either slightly soluble or insoluble in water
      (ii) the release rate of the active ingredient from the formulation is accelerated in a body fluid, and
      (iii) wherein the hydrophobic polymer comprises a non-biodegradable polymer.

2. A sustained-release formulation for implantation, which comprises one of particle combinations, which is selected from the group consisting of (a), (b) and (c), and a carrier comprising a hydrophobic polymer, wherein the particle combination is dispersed in the carrier, and wherein the formulation has a shape selected from the group consisting of cylindrical, prismatically cylindrical, cylindroid, tabular, and spherical shape:
   (a) a particle combination which comprises particles comprising an active ingredient, particles comprising a carbonate, and particles comprising a substance which reacts with the carbonate in an aqueous solution to generate carbon dioxide;
   (b) a particle combination which comprises particles comprising an active ingredient and a carbonate, and particles comprising a substance which reacts with the carbonate in an aqueous solution to generate carbon dioxide; and
   (c) a particle combination which comprises particles comprising a carbonate, and particles comprising an active ingredient and a substance which reacts with the carbonate in an aqueous solution to generate carbon dioxide; and
   wherein
      (i) the active ingredient is either slightly soluble or insoluble in water,
      (ii) and the release rate of the active ingredient from the formulation is accelerated in a body fluid, and
      (iii) wherein the hydrophobic polymer comprises a non-biodegradable polymer.

3. The sustained-release formulation as claimed in claim 1 or 2, wherein the active ingredient is an insoluble ingredient.

4. The sustained-release formulation as claimed in claim 3, wherein the insoluble ingredient comprises a live vaccine, or an inactivated vaccine.

5. The sustained-release formulation as claimed in claim 1 or 2, wherein the hydrophobic polymer comprises silicone.

6. The sustained-release formulation as claimed in claim 1 or 2, wherein the active ingredient is a slightly soluble ingredient.

* * * * *